(12) United States Patent
Moore et al.

(10) Patent No.: US 8,357,767 B2
(45) Date of Patent: Jan. 22, 2013

(54) HIGH MODULUS POLYURETHANE AND POLYURETHANE/UREA COMPOSITIONS

(75) Inventors: Timothy Graeme Moore, Braybrook (AU); Pathiraja Arachchillage Gunatillake, Mulgrave (AU); Raju Adhikari, Wheelers Hill (AU); Shadi Houshyar, Doncaster East (AU)

(73) Assignee: Polynovo Biomaterials Limited, Clayton (AU)

( * ) Notice: Subject to any disclaimer, the term of this patent is extended or adjusted under 35 U.S.C. 154(b) by 167 days.

(21) Appl. No.: 12/245,491

(22) Filed: Oct. 3, 2008

(65) Prior Publication Data

US 2009/0099600 A1  Apr. 16, 2009

(30) Foreign Application Priority Data

Oct. 3, 2007  (AU) ............... 2007905409

(51) Int. Cl.
C08G 18/66 (2006.01)
C08G 18/72 (2006.01)
(52) U.S. Cl. ............... 528/76; 528/67; 528/80; 528/85
(58) Field of Classification Search ............ 528/67
See application file for complete search history.

(56) References Cited

U.S. PATENT DOCUMENTS

| | | | |
|---|---|---|---|
| 3,007,899 A | 11/1961 | Urs | 528/76 |
| 3,247,282 A | 4/1966 | Englisch | 528/306 |
| 3,281,378 A | 10/1966 | Garber et al. | 260/2.5 |
| 3,360,546 A | 12/1967 | Wygant et al. | 560/191 |
| 4,035,274 A | 7/1977 | McGinniss | 522/9 |
| 4,192,827 A | 3/1980 | Mueller et al. | 525/123 |
| 4,273,690 A | 6/1981 | Walus | 525/7 |
| 4,284,506 A * | 8/1981 | Tetenbaum et al. | 210/321.6 |
| 4,293,679 A | 10/1981 | Cogliano | 528/48 |
| 4,412,033 A | 10/1983 | LaBelle et al. | 524/590 |
| 4,424,252 A | 1/1984 | Nativi | 428/209 |
| 4,438,253 A * | 3/1984 | Casey et al. | 528/86 |
| 4,451,523 A | 5/1984 | Nativi et al. | 428/209 |
| 4,908,406 A | 3/1990 | Mulhaupt et al. | 525/64 |
| 4,935,480 A | 6/1990 | Zdrahala et al. | 528/28 |
| 5,041,516 A | 8/1991 | Frechet et al. | 528/44 |
| 5,109,077 A | 4/1992 | Wick | 525/467 |
| 5,276,068 A | 1/1994 | Waknine | 522/28 |

(Continued)

FOREIGN PATENT DOCUMENTS

EP  837084  4/1998

(Continued)

OTHER PUBLICATIONS

Restriction Requirement dated Apr. 2, 2009 (Polynovo Biomaterials Pty Ltd. U.S. Appl. No. 11/087,561).

(Continued)

*Primary Examiner* — Randy Gulakowski
*Assistant Examiner* — Mike M Dollinger
(74) *Attorney, Agent, or Firm* — Connolly Bove Lodge & Hutz LLP

(57) ABSTRACT

The present invention provides a polyurethane or polyurethane/urea composition which has a tensile strength greater than 10 MPa, a modulus of elasticity greater than 400 MPa and an elongation at break greater than 30% at a temperature of between 0° C. and 60° C. and at a relative humidity of between 0% and 100%. The invention further provides uses of the compositions of the invention in biomedical vascular stents, an orthopedic implant, a drug delivery coating or in tissue engineering.

24 Claims, 1 Drawing Sheet

DSC thermogram of polymer prepared in Example 3.

U.S. PATENT DOCUMENTS

| | | | | |
|---|---|---|---|---|
| 5,578,662 | A | 11/1996 | Bennett et al. | 524/54 |
| 5,886,127 | A | 3/1999 | Newkome et al. | 528/49 |
| 5,981,684 | A | 11/1999 | Bruchmann et al. | 528/45 |
| 6,124,370 | A | 9/2000 | Walton et al. | 521/143 |
| 6,150,438 | A | 11/2000 | Shiraishi et al. | 524/35 |
| 6,262,296 | B1 * | 7/2001 | Nomura et al. | 560/115 |
| 6,376,637 | B1 | 4/2002 | Bruchmann et al. | 528/60 |
| 6,376,742 | B1 | 4/2002 | Zdrahala et al. | 623/11.11 |
| 6,388,047 | B1 | 5/2002 | Wan et al. | 528/354 |
| 6,756,468 | B2 * | 6/2004 | Turri et al. | 528/66 |
| 6,797,798 | B2 * | 9/2004 | Johnston | 528/60 |
| 7,193,011 | B2 * | 3/2007 | Kim et al. | 524/591 |
| 2001/0005738 | A1 | 6/2001 | Bruchmann et al. | 525/123 |
| 2002/0103347 | A1 | 8/2002 | Isaka et al. | 530/413 |
| 2003/0153673 | A1 | 8/2003 | Schwalm et al. | 524/589 |
| 2004/0097684 | A1 | 5/2004 | Bruchmann et al. | 528/44 |
| 2005/0112203 | A1 | 5/2005 | Shau et al. | 424/489 |
| 2006/0074208 | A1 | 4/2006 | Laredo | 526/279 |

FOREIGN PATENT DOCUMENTS

| | | |
|---|---|---|
| EP | 03 739 861.7 | 1/2008 |
| JP | 07-070296 | 3/1995 |
| WO | WO 99/02168 | 1/1999 |
| WO | WO 00/12579 | 3/2000 |
| WO | WO 00/67813 | 11/2000 |
| WO | WO 02/09655 | 2/2002 |
| WO | WO 02/10247 | 2/2002 |
| WO | WO 02/10292 | 2/2002 |
| WO | WO 2004/065450 | 8/2004 |
| WO | WO 2005/089778 | 9/2005 |
| WO | WO 2006/010278 | 2/2006 |

OTHER PUBLICATIONS

Restriction Requirement dated Nov. 28, 2007 (Polynovo Biomaterials Pty Ltd. U.S. Appl. No. 11/070,217).
Response dated Dec. 26, 2007 (Polynovo Biomaterials Pty Ltd. U.S. Appl. No. 11/070,217).
Non-Final Office Action dated Mar. 27, 2008 (Polynovo Biomaterials Pty Ltd. U.S. Appl. No. 11/070,217).
Response dated Jul. 28, 2008 (Polynovo Biomaterials Pty Ltd. U.S. Appl. No. 11/070,217).
Final Rejection dated Oct. 30, 2008 (Polynovo Biomaterials Pty Ltd. U.S. Appl. No. 11/070,217).
Response to Final Office Action Jan. 30, 2009 (Polynovo Biomaterials Pty Ltd. U.S. Appl. No. 11/070,217).
Advisory Action Mar. 21, 2009 (Polynovo Biomaterials Pty Ltd. U.S. Appl. No. 11/070,217).
Preliminary Amendment dated Sep. 25, 2006 (Polynovo Biomaterials Pty Ltd. U.S. Appl. No. 10/520,414).
Restriction Requirement dated Sep. 12, 2007 (Polynovo Biomaterials Pty Ltd. U.S. Appl. No. 10/520,414) (Polynovo Biomaterials Pty Ltd. U.S. Appl. No. 10/520,414).
Response dated Oct. 12, 2007 (Polynovo Biomaterials Pty Ltd. U.S. Appl. No. 10/520,414).
Non-Final Action dated Nov. 29, 2007 (Polynovo Biomaterials Pty Ltd. U.S. Appl. No. 10/520,414).
Response to Non-Final Action dated Feb. 29, 2008 (Polynovo Biomaterials Pty Ltd. U.S. Appl. No. 10/520,414).
Final Office Action dated May 29, 2008 (Polynovo Biomaterials Pty Ltd. U.S. Appl. No. 10/520,414).
Response to Final Office Action dated Nov. 12, 2008 (Polynovo Biomaterials Pty Ltd. U.S. Appl. No. 10/520,414).
Office Action dated Feb. 3, 2009 (Polynovo Biomaterials Pty Ltd. U.S. Appl. No. 10/520,414).
Arroyo et al. Revista de Plasticos Modernos, 218:217-226, 1974.
Yoshida et al. Agricultural and Biological Chemistry 34(11):1668-1675.
Ogata et al., Biochemica et Biophysica Acta, 742:384-390, 1983.
STN Database, File Registry, Registry No. 57214-23-0.
STN Database, File CA, Accession No. AN 82:113308.

* cited by examiner

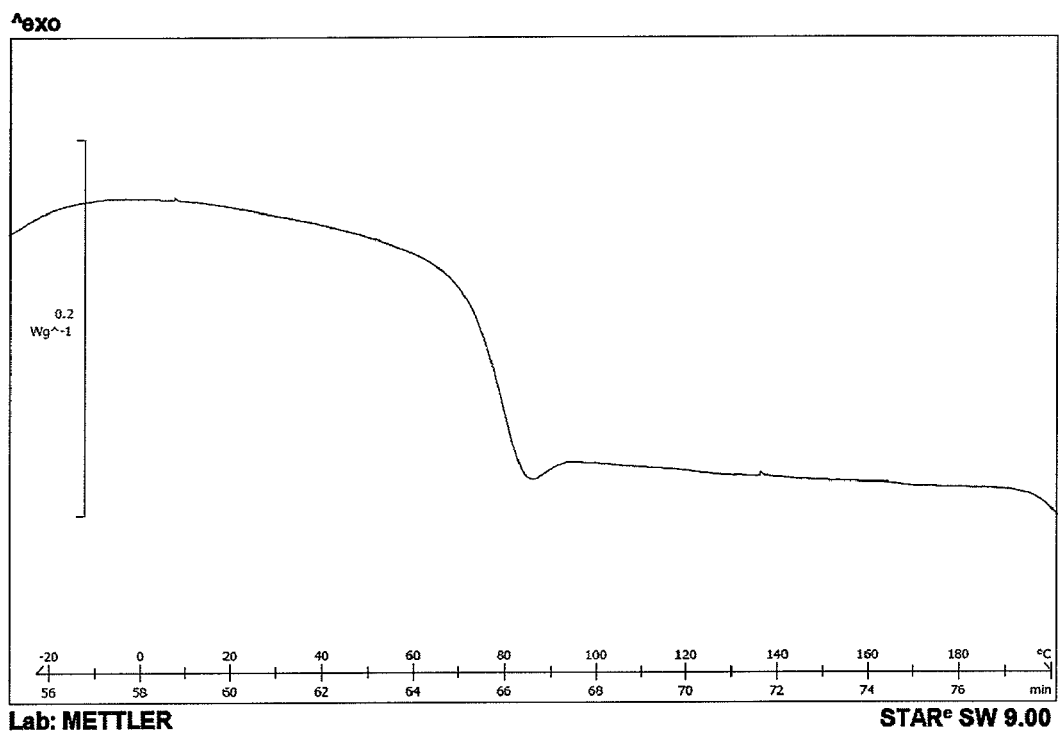
DSC thermogram of polymer prepared in Example 3.

HIGH MODULUS POLYURETHANE AND POLYURETHANE/UREA COMPOSITIONS

CROSS-REFERENCE TO RELATED APPLICATIONS

This application claims benefit of priority to Australian Provisional Application No. 2007905409 filed Oct. 3, 2007, which is herein incorporated by reference in its entirety.

FIELD OF INVENTION

The present invention relates to processable polyurethane and polyurethane/urea compositions having high modulus, high strength and high elongation. The compositions are particularly useful as biocompatible biodegradable implants that require the retention of mechanical strength until such time that the tissue regeneration/repair process is complete. The compositions can be used in scaffolds for tissue engineering, orthopedic fixation, vascular stents, and bone substitutes or scaffolds.

BACKGROUND

Synthetic biomedical polymers can be broadly classified into non-biodegradable and biodegradable polymers. Those that are non-biodegradable are widely used when a medical device needs to be in place indefinitely or until such time as it is decided that the device is no longer required and can be safely removed, i.e. in permanent fixation devices. These polymers need to be completely non-biodegradable or have minimal degradation properties in the environment in which they are placed and are, for example, widely used in areas such as breast implants, in orthopedic applications such as bone fixation devices and, more recently, to replace important tissues such as heart valves. Polysiloxanes, polyurethanes and or their copolymers are widely used in such applications. Other examples include polyesters such as Dacron and polyetherether ketones (PEEK).

On the other hand, biodegradable polymers provide mechanical support and act as a platform for biological tissues to regenerate or repair when used in vivo and degrade after a period of time depending on the type of biodegradable polymer and the tissue environment. For these reasons, biodegradable polymers are particularly useful in orthopedic applications and tissue engineered products and therapies.

The vast majority of biodegradable polymers studied belong to the polyester family. Among these poly($\alpha$-hydroxy acids) such as poly(glycolic acid), poly(lactic acid) and a range of their copolymers have historically comprised the bulk of published material on biodegradable polyesters and have a long history of use as synthetic biodegradable materials in a number of clinical applications. Among these applications, poly(glycolic acid), poly(lactic acid) and their copolymers, poly(p-dioxanone), and copolymers of trimethylene carbonate and glycolide have been the most widely used. Their major applications include resorbable sutures, drug delivery systems and orthopedic fixation devices such as pins, rods and screws. Among the families of synthetic polymers, the polyesters have been attractive for use in these applications because of their ease of degradation by hydrolysis of their ester linkage, the fact that their degradation products are resorbed through metabolic pathways in some cases and their potential to be tailored in terms of their structure to alter degradation rates.

Synthetic polymers offer the advantage of tailoring the mechanical and other properties required for an intended application by choosing appropriate monomers and monomer combinations. Accordingly, various co-polymerisation methods have been developed to prepare polymers with a broad range of mechanical properties from the polyester family. Copolymers of lactic, glycolic acid, and $\epsilon$-caprolactone are a few examples.

Most high modulus and high strength polymers are generally very brittle and have elongation at failure around 10% or less. Examples include poly(lactic acid), poly(glycolic acid), and polyanhydrides. Similarly, high modulus biostable polymers such as PEEK and ElastEon 4 (U.S. Pat. No. 6,437,073 B1) have failure elongations less than 50%.

Various strategies have been employed to improve the toughness of synthetic polymers. One of the main strategies employed is rubber toughening, incorporation of micron size rubber particle to brittle amorphous polymers [J Appl Polym Sci, 76, 1074 (2000)]. This approach has the disadvantage of having to incorporate a second polymer which is not desirable for many medical implant applications due to incompatibility and mechanical property mismatch. Furthermore, the improvement in elongation comes with a compromise in modulus and strength. Similarly, the incorporation of inorganic fillers increases modulus but with a compromise in elongation and strength, and such materials are not desirable for medical implant applications where high elongation is required.

High strength biodegradable polymers are sought after for applications such as vascular stents, fracture fixation implants and in other orthopedic applications such as spinal cages. High modulus but less brittle materials that can hold mechanical properties for a period of time until the repair process is completed are particularly sought after. For example, in coronary stents after the balloon expansion of the affected region of the blood vessel, the mechanical support of the stent is required for several months allowing sufficient time for the damaged vessel to repair. During this period the cellular growth around the stent takes place to rebuild the damaged vessel. The retention of material properties under physiological conditions (37° C., in vivo) is required for such applications. Accordingly, it is critical that the materials have high modulus, strength and elongation to prevent the implant from brittle failure for optimum performance of the implant in the biological environment.

Polyurethanes as a class of synthetic polymers offer advantages over other classes of polymers in designing materials with such properties. A wide range of polymers with a variety of properties ranging from elastomers to rigid materials can be prepared by selecting a suitable combination of reagents in various proportions. Diisocyanates, polyols and chain extenders are the three main reagents used to prepare polyurethanes. A high proportion of the diisocyanate and the chain extender generally yield rigid polyurethanes with high modulus and high strength. The polyurethane formed by reacting only the chain extender and the diisocyanate are generally very rigid with high modulus but very brittle and difficult to thermally process. For example, a polyurethane prepared from 4,4'-methylenediphenyldiisocyanate (MDI) and 1,4-butanediol (BDO) is very brittle due to its high crystallinity and melts above 210° C. [Polyurethanes Chemistry, Technology and Applications, Ellis Harwood p 118 (1993)]. Further, such materials have high modulus but due to brittleness have very limited applications.

The incorporations of fillers, rubber toughening, polymer blending have been reported in the polyurethane literature as methods to improve the toughness [see, for example, J Appl Polym Sci, 76, 1074, (2000); Polymer, 39, 865, (1998); Macromolecules, 30, 2876, (1997); J Appl Polym Sci, 63, 1335, (1997); J Appl Polym Sci, 63, 1865, (1997); WO 2006010278]. Results of these studies show that the increase in elongation to failure (increased toughness) always comes with a reduction in elastic modulus. In most cases the failure elongation was less than 5%.

In medical implants such as spinal cages and vascular stents the retention of the initial strength of the material is crucial for the proper function of the implant. Brittle materials will fail due to motion or other forces present in the biological system. Likewise, materials used for implants in bone fracture fixation not only should have sufficient mechanical strength to stabilise the fixation but also should retain the strength for a period of time ranging from weeks to months for proper healing of the damaged bone.

Accordingly, one object of this invention is to develop polymer compositions with high modulus, high strength and high elongation at failure for applications requiring load bearing capabilities. Desirably the compositions are biocompatible and capable of retaining initial mechanical properties under physiological conditions until the regenerated tissue structure can develop sufficient mechanical properties and subsequently the polymer degrades when no further mechanical support is required.

SUMMARY OF INVENTION

To this end, the present invention provides a polyurethane or polyurethane/urea composition which has a tensile strength greater than 10 MPa, a modulus of elasticity greater than 400 MPa and an elongation at break greater than 30% at a temperature of between 0° C. and 60° C. and at a relative humidity of between 0% and 100%.

Preferably the polyurethane or polyurethane/urea composition has an elongation at break of greater than 75% at a temperature of between 0° C. and 60° C. and at a relative humidity of between 0% and 100%.

More preferably the polyurethane or polyurethane/urea composition has an elongation at break of greater than 150% at a temperature of between 0° C. and 60° C. and at a relative humidity of between 0% and 100%.

In a preferred embodiment the polyurethane or polyurethane/urea composition comprises at least two polyurethanes and/or polyurethane/ureas having different glass transition temperatures (Tg). This is preferably achieved by the use of combinations of diisocyanates. This polyurethane or polyurethane/urea composition may be formed in situ or, alternatively, through blending the at least two polyurethanes or polyurethane/ureas, and in so doing polyurethanes or polyurethane/ureas having the mechanical properties of this embodiment are obtained.

In a further preferred embodiment of the present invention the polyurethane or polyurethane/urea composition is derived from at least two diisocyanates wherein at least one of the diisocyanates contains isocyanate moieties in an unsymmetric configuration.

In a particularly preferred form of this embodiment of the invention at least one of the diisocyanates contains isocyanate moieties in a symmetric configuration and at least one of the diisocyanates contains isocyanate moieties in an unsymmetric configuration.

The term "symmetrical" refers to structural symmetry with respect to the two isocyanate functional groups within the diisocyanate structure. In such compounds a line of symmetry or plane of symmetry exists and as such has the potential to form ordered or crystalline hard segments in polyurethane or polyurethane/ureas.

In an alternate preferred embodiment of the present invention the polyurethane or polyurethane/urea composition is derived from at least one diisocyanate containing isocyanate moieties attached to a cyclic structure.

In a particularly preferred form of this embodiment of the invention the polyurethane or polyurethane/urea composition is derived from at least one diisocyanate containing isocyanate moieties attached to a linear structure.

In any embodiment of the invention the polyurethane or polyurethane/urea compositions preferably comprise a mixture of two or more diisocyanates, one or more polyols and one or more chain extenders.

At least one of the chain extenders may be one containing a hydrolysable functional group.

The compositions according to the invention are preferably biocompatible, and more preferably biodegradable.

It has been found that the compositions according to the invention are particularly useful in applications where high modulus, high strength and high elongation are desired, for example, in applications requiring high load bearing capacity, such as, for example, medical devices.

It has also been found that the compositions according to the invention retain the properties of high modulus, high strength and high elongation under physiological conditions (37° C., in vivo) providing an advantage for use in such biomedical applications. For example, in providing an implant for use as a vascular stent the compositions according to the invention retain the material properties for periods of time sufficient to allow tissue growth and repair to occur. Further, in providing an implant in a physically demanding application, such as a spinal cage, for example, the compositions retain mechanical strength and also provide flexibility so that brittle failure is minimised.

The compositions according to the invention are also biodegradable, such that after a period of time under physiological conditions the compositions degrade to biocompatible degradation products.

Preferably the compositions according to the invention have a tensile strength in the range of 10 to 100 MPa, elastic modulus in the range 400 MPa to 3000 MPa and elongation at failure in the range 30 to 400% at a temperature between 0° C. and 60° C. and at a relative humidity of between 0% and 100%. More preferably the polyurethane or polyurethane/urea compositions have an elongation at failure in the range 75% to 400% at a temperature of between 0° C. and 60° C. and at a relative humidity of between 0% and 100%. Most preferably the polyurethane or polyurethane/urea compositions have an elongation at failure of between 150% and 400% at a temperature of between 0° C. and 60° C. and at a relative humidity of between 0% and 100%.

It is further preferred that the compositions retain the initial properties in a physiological environment (37° C., in vivo) for a period of one week or longer.

In another aspect of the invention, there is provided a use of any of the polyurethanes and polyurethane/urea compositions according to the invention in biomedical vascular stents which are preferably biodegradable. Bioactive agents such as anti-thrombolytic, anti-inflammatory or antiproliferative can be incorporated as a coating on the stent or blended with the polymer. Examples of biological agents include paclitaxel, rapamycin, and heparin.

In yet another aspect of the invention there is provided a use of any of the polyurethanes and polyurethane/urea compositions according to the invention in orthopedic implants which are preferably biodegradable. Examples include spinal cages, fracture fixation hardware including fixation plates, screws, pins or rods.

In yet another aspect of the invention, there is provided a use of any of the polyurethane and polyurethane/urea compositions according to the invention in drug delivery coatings.

In yet another aspect of the invention, there is provided a use of any of the polyurethanes and polyurethane/urea compositions according to the invention in tissue repair or engineering in a patient requiring such treatment the use comprising inserting in said patient the biocompatible, biodegradable polyurethane or polyurethane/urea scaffolds according to the invention prepared by rapid prototyping techniques such as, but not limited to, fused deposition modeling. The polyurethane or polyurethane/urea may preferably include biological additives to assist for example in the repair of the damaged bone or cartilage such as cells, progenitor cells, growth factors, or other suitable materials or other additives, such as pharmaceuticals for use in drug delivery. Biological additives used may preferably include osteoblasts, chondrocytes, fibroblasts, fibrin, collagen, transglutaminase systems and the like.

The invention also provides for the use of biocompatible, biodegradable polyurethanes and polyurethane/urea compositions according to the invention as a tissue engineering scaffold for assistance in tissue engineering applications such as, for example, as a scaffold in bone and cartilage repair.

There is also provided an article of manufacture formed from any of the polyurethane or polyurethane/urea compositions according to the invention. The article may be a medical device, a bone fixation device, a stent, a spinal cage, a medical implant or a scaffold.

Other embodiments of the invention will be evident from the following detailed description of various aspects of the invention.

Throughout this specification the terms "comprises" or "comprising" or grammatical variations thereon shall be taken to specify the presence of stated features, integers, steps or components but does not preclude the presence or addition of one or more other features, integers, steps, components or groups thereof not specifically mentioned.

BRIEF DESCRIPTION OF THE DRAWINGS

The accompanying drawings illustrate certain embodiments of the disclosure.

FIG. 1 illustrates a differential scanning calorimetry (DSC) trace for an exemplary polymer according to Example 3 as described herein.

DETAILED DESCRIPTION OF THE INVENTION

Isocyanates suitable for the preparation of the polyurethane or polyurethane/urea compositions of the invention are those which are selected from the group consisting of symmetrical and unsymmetrical diisocyanates.

Symmetrical diisocyanates suitable for the preparation of the polyurethanes or polyurethane/urea compositions of the invention are those which are selected from the group consisting of unsubstituted linear or cyclic aliphatic, substituted or unsubstituted aromatic and hindered diisocyanates. Examples of symmetrical diisocyanates include:
1. 1,6-hexamethylene diisocyanate
2. trans-cyclohexane diisocyanate
3. 1,4-butanediisocyanate
4. 1,2-ethanediisocyanate
5. 1,3-propanediisocyanate
6. para-tetramethyl xylene diisocyanate
7. 4,4'-methylene diphenyldiisocyanate
8. 1,4-naphthalene diisocyanate
9. para-phenylene diisocyanate
10. 4,4'-methylene-bis(cyclohexyl isocyanate)
11. meta-tetramethyl xylenediisocyanate
12. cis-cyclohexanediisocyanate The corresponding isothiocyanates are also suitable symmetrical diisocyanates and examples include 1,4-butane diisothiocyanate and 1,6-hexane diisothiocyanate.

Unsymmetrical diisocyanates suitable for preparation of the polyurethanes or polyurethane/urea compositions of the invention are those which are selected from the group consisting of substituted linear or cyclic aliphatic, substituted or unsubstituted aromatic and hindered diisocyanates. The diisocyanates do not have structural symmetry with respect to the two isocyanate functional groups within the structure and as such typically forms amorphous or less ordered hard segment structures in polyurethane/ureas. Examples of Unsymmetrical Diisocyanates Include
1. isophorone diisocyanate
2. toluene diisocyanate
3. lysine diisocyanate ethyl ester
4. lysine diisocyanate methyl ester
5. 2,4,4,-trimethyl 1,6-hexane diisocyanate Iocyanates further suitable for the preparation of the polyurethane or polyurethane/urea compositions of the invention are those in which the isocyanate moiety is attached to a cyclic structure. Such isocyanates may be symmetric or unsymmetric.

Combinations of cyclic and linear diisocyanates have been found to produce polyurethanes and polyurethane/urea compositions with particularly desirable properties. For example trans-cyclohexane diisocyanate (symmetric) or isophorone diisocyanate (unsymmetric) produce polyurethanes or polyurethane/ureas with a high glass transition temperature whereas 1,6-hexamethylene diisocyanate (symmetric) produces polyurethanes or polyurethane/ureas with a low glass transition temperature. By blending, or by generating in situ, polyurethanes or polyurethane/ureas with high and low glass transition temperatures, using either the aforementioned diisocyanates or other suitable diisocyanates, compositions with desirable mechanical properties result.

Throughout this specification, the term "polyol" should be taken to mean a molecule which has at least two or more functional hydroxyl groups that can react with isocyanate groups to form urethane groups. Examples of polyols include but are not limited to diols, triols, and polyols such as macrodiols. The polyols may be condensation reactions products of hydroxy acids, hydroxy acids with diol initiators or dicarboxylic acids with diols. The polyol may be terminated by, for example, a hydroxyl, thiol or carboxylic acid group.

The structure of the polyol is preferably:

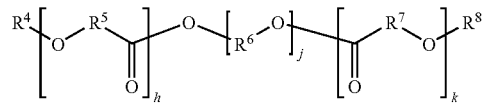

in which h and/or k can equal 0 or are integers as is j and $R^4$ and $R^9$ are independently selected from hydrogen, hydroxylalkyl, aminoalkyl, (both primary and secondary) and carboxy alkyl and $R^6$, $R^5$ and $R^7$ cannot be hydrogen, but can independently be a linear or branched alkyl, alkenyl, aminoalkyl, alkoxy or aryl. $R^5$ and $R^7$ can be the same or different and distributed alternately, randomly or as blocks with the polyol structure.

The molecular weight of the polyol is preferably 350 to 3000 and more preferably 350 to 1500.

For example, the polyol can be prepared from a hydroxyl acid such as glycolic acid and 1,4-butanediol:

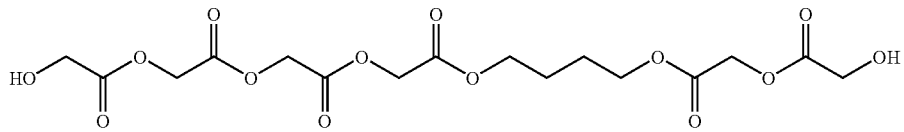

where $R^5$ and $R^7$ are —$CH_2$—, $R^6$ is —$CH_2$—$CH_2$—, $R^4$ and $R^8$ are H, j=1, h+k=5.4 and the average molecular weight of the polyol is 438.34.

Similarly a polyol containing segments derived from more than one hydroxy acid could be prepared by reacting ε-caprolactone, lactic acid and ethylene glycol. The following structure illustrates a copolymer polyol an average molecular weight of 620.68:

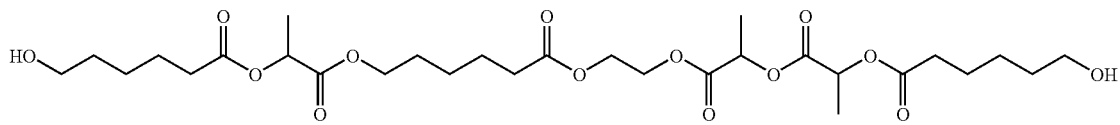

where $R^5$ and $R^7$ are (CH—$CH_3$) and $(CH_2)_5$, respectively but randomly distributed within the polyol structure. $R^6$ is —$CH_2$—$CH_2$—, $R^4$ and $R^8$ are H, j=1, h+k=6.

Polyols derived from condensation of dicarboxylic acids such as succinic acid and 1,4-butanediol are also useful for preparing polyurethanes and polyurethane ureas according to the invention.

Examples of other polyols which may act as soft segments include poly-(4-hydroxybutyrate) diol (P4HB diol), poly-(3-hydroxybutyrate) diol (P3HB diol), polypropylene glycol and any copolymers thereof including PLGA diol, P(LA/CL) diol and P(3HB/4HB) diol.

Polyether polyols such as poly(tetramethylene oxide), polycarbonate polyols such as poly(hexamethylene carbonate) diol may also be used as soft segment forming polyols.

Throughout this specification, the term "chain extender" should be taken to mean a low molecular weight compound having two or more functional groups that are reactive towards isocyanate and having a molecular weight of less than 350. Examples of reactive functional groups include hydroxyl (OH), amine ($NH_2$), carboxyl (COOH) and thiol (SH). The conventional chain extender is preferably difunctional and may be diols, dithiols, diamines, amino acids, hydroxylamines, hydroxyl acids or dicarboxylic acids. Examples of diols include ethylene glycol, diethylene glycol, tetraethylene glycol, 1,3-propane diol, 1,4-butane diol, 1,6-hexanediol, 1,7-heptanediol, 1,8-octanediol, 1,9-nonanediol, 1,10-decanediol. Examples of diamines and amino acids include 1,4-butanediamine, ethylenediamine, 1,3-propanediamine, 1,6-hexanediamine, isophoronediamine, glycine. Examples of hydroxylamines include ethanolamine, 2-butylamino ethanol, propanol amine N-methyldiethanolamine, N-alkyldiethanolamines and examples of dithiols such as alkyldithiols, i.e. ethane or propane dithiol. The chain extender can also include trifunctional amino acids such as lysine.

Chain extenders also include functional monomers with degradable or hydrolysable backbones. The chain extender may be employed to introduce easily degradable hard segment components into the polyurethane or polyurethane/urea structure. Incorporating such chain extenders allows preparation of easily degradable polyurethanes with fewer degradation products. For example, polyurethane based on ethyl-lysine diisocyanate and glycolic acid based polyol and chain extender based on glycolic acid and ethylene glycol degrades to glycolic acid, lysine, ethylene glycol, carbon dioxide and ethanol.

Degradable chain extenders of the present invention have one or more hydrolysable (degradable) functional groups in the backbone. The term "hydrolysable (degradable) functional group" refers to any molecular moiety which may be part of the chain extender and is preferably biocompatible and bioresorbable on in vivo degradation of the biocompatible biodegradable polyurethane or polyurethane urea which is formed from the chain extender.

Degradable chain extenders of the present invention are based on ester diols of α-hydroxy acids or dicarboxylic acids which optionally contain free radically polymerisable functional group(s) in the backbone. When these chain extenders are used either alone or in combination with conventional chain extenders to form polyurethanes or polyurethane ureas, the polyurethanes degrade at faster rates than those based on conventional chain extenders. Furthermore, the polyurethanes or polyurethane ureas degrade to low molecular weight compounds due to the degradation of the hard segment which is formed from the chain extenders of the present invention at rates comparable to that of the soft segment which results in minimum levels of oligomeric hard segment species among the degradation products. The chain extenders based on ester diols of dicarboxylic acids provide two hydrolysable (degradable) functional groups within the chain extender backbone to facilitate even faster break down of the hard segment structure. The presence of a free radically polymerisable functional group in the backbone also facilitates cross linking of the hard segment. Polyurethanes or polyurethane ureas based on these chain extenders can be processed and subsequently cross linked to form network structures with improved mechanical properties.

Preferred degradable chain extenders have the formula (Ia) and (Ib) shown below:

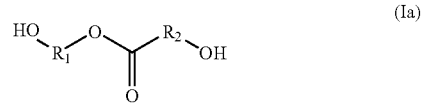

(Ia)

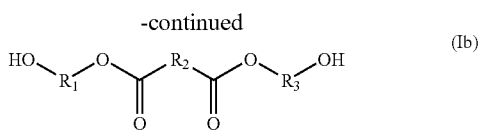

in which R1, R2 and R3 are independently selected from optionally substituted C1-20 alkylene and optionally substituted C2-20 alkenylene both of which may be optionally interrupted by optionally substituted aryl or optionally substituted heterocyclyl, preferably optionally substituted C1-6 alkylene or optionally substituted C2-6 alkenylene.

Representative examples of a compound of formula (Ia) are as follows:

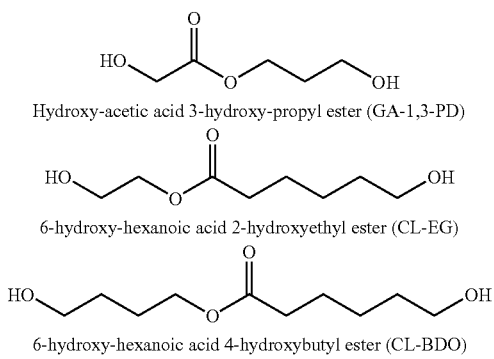

Representative examples of a compound of formula (Ib) are as follows:

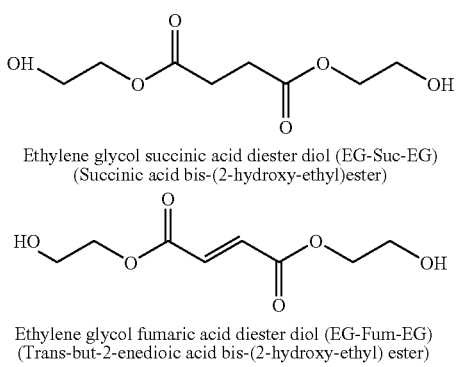

A preferred composition according to the present invention is produced from a polyol, a chain extender and at least two diisocyanates.

More preferably the at least two diisocyanates are different. Most preferably at least one of the diisocyanates contains isocyanate moieties in a symmetric configuration and least one of the diisocyanates contains isocyanate moieties in an unsymmetric configuration. Alternatively, at least one of the diisocyanates contains isocyanate moieties attached to a cyclic structure. In this alternate embodiment preferably at least one of the diisocyanates contains isocyanate moieties attached to a linear structure.

The "hard segment" derived from a mixture of diisocyanates and a chain extender according to the invention is one which imbues the copolymer with its physical strength.

Where the hard segment represents 100% by weight, the chain extender has a dual functionality of being both the chain extender and polyol.

The polyurethanes and polyurethane/urea compositions can be prepared using both bulk and solution polymerisation procedures. Bulk polymerisation is the preferred option and one-step, two-step or reactive extrusion methods can be used to synthesise polymers. In the one-step process all ingredients are mixed together in one pot and thoroughly mixed to form a homogeneous mixture and cured subsequently to complete the polymerisation process. In a two-step process the polyol and/or part of the chain extender is mixed with the diisocyanate mixture and the remaining chain extender is added in a second step, thoroughly mixed and cured to complete the polymerisation.

The polyurethanes and polyurethane/urea compositions can be prepared with mixtures of different diisocyanates, for example, a symmetric and an unsymmetric diisocyanate or a cyclic and a linear diisocyanate. The diisocyanates can be premixed and added to the polyol together. Alternatively, the symmetric diisocyanate can be first added to the polyol followed by the unsymmetric diisocyanate, or vice versa. Similar variations may apply to the use of cyclic and linear diisocyanates. These variations in preparation method can provide control over the properties and morphology of the "hard segment".

The hard segment may represent 40 to 100% by weight of the polyurethane/polyurethane/urea. More preferably the hard segment represents 60 to 100% by weight. The polyol and chain extender may be the same compound and this corresponds to the embodiment where the hard segment corresponds to 100% by weight of the polyurethane/polyurethane/urea. It has also been found that there must be a reasonably high proportion of hard segment for the materials to have adequate properties to meet the property specifications for the intended application.

The polyurethanes and polyurethane/urea compositions can be prepared by blending mixtures of polyurethanes and polyurethane/ureas prepared with different diisocyanates. Thus compositions prepared separately using an unsymmetric and a symmetric diisocyanate for example may be coextruded to provide a composition according to the invention. Similarly, polyurethanes or polyurethane/ureas may be prepared separately using cyclic and linear diisocyanates and the compositions prepared by blending.

Optionally a catalyst or a combination of two or more catalysts may be incorporated to speed up the polymerisation reaction. Preferred catalysts include stannous octoate (stannous 2-ethyl hexanoate), dibutyltin dilaurate, 1,4-diazabicyclo[2.2.2] octane and triethylamine. Other catalysts that may be useful include tetra n-butyl titanate, titanium acetylacetonate, triethanolamine titanate, titanium ethylaceto-acetate, tetraethyl titanate, tetraisopropyl titanate, titanium lactic acid chelate and other catalysts available under the TYZOR range from DuPont.

The polyurethanes and polyurethane/urea compositions can be sterilised without risk to their physical and chemical characteristics, preferably using gamma radiation to ensure sterility. Other common sterilisation methods such as ethylene oxide treatment can be used to sterilise the polymer or implants or other articles prepared from the polymer.

The polyurethanes can be easily processed using known techniques such as extrusion, injection and compression molding. The polyurethanes are soluble in a range of common organic solvents including, THF, chloroform, methylene chloride, N,N-dimethyl formamide (DMF), N,N-dimethyl acetamide (DMAC). Accordingly, the polymers can be used to prepare coatings on medical implants. For example, the polymer may be used as a drug delivery coating on stents.

The polyurethanes can also be made radio opaque by incorporating radio opaque substances such as barium sulfate, barium carbonate or halogen-containing compounds or fillers such as tricalcium phosphate and hydroxyapatite. These compounds can be incorporated to the polyurethane at the time of polymer synthesis or during processing such as extrusion. Incorporation of radio opaque markers such as gold can also be incorporated to the fabricated implant at different positions to make the implant radio opaque.

Preferably the cured scaffolds made according to the invention have a tensile strength in the range of 10 to 100 MPa, elastic modulus in the range 400 MPa to 3000 MPa and elongation at failure in the range 30 to 400% when tested at a temperature between 0° C. and 60° C. and at a relative humidity of between 0% and 100%. It is further preferred that the scaffold retain their initial physical properties in a physiological environment (37° C., in vivo) for a period of one week or longer. More preferably the cured scaffolds have an elongation at failure in the range 75% to 400% at a temperature of between 0° C. and 60° C. and at a relative humidity of between 0% and 100%. Most preferably the cured scaffolds have an elongation at failure of between 150% and 400% at a temperature of between 0° C. and 60° C. and at a relative humidity of between 0% and 100%.

In one composition according to the invention, the polyol is a lactic acid-co-glycolic acid polyol of molecular weight 1033.1, the chain extender is 1,4-butanediol and the isocyanates are a mixture of 1,6-hexamethylenediisocyanate and isophorone diisocyanate.

In another composition according to the invention, the polyol is a poly-DL-lactic acid of molecular weight 1027.33, the chain extender is 1,4-butanediol and the isocyanates are a mixture of 1,6-hexamethylenediisocyanate and isophorone diisocyanate.

The following examples are intended to illustrate the scope of the invention and to enable reproduction and comparison. They are not intended to limit the scope of the disclosure in any way.

EXAMPLES

Example 1

This example illustrates the preparation of a polyurethane series with hard segment weight percentage of 60, 70, 80, 90, and 100% using an 80/20 (molar) mixture of IPDI and HDI. The soft segment was LLA-GA (90:10 molar) polyol with a molecular weight of 1033.1 and the chain extender was 1,4-butanediol (BDO).

Step 1: Preparation of Lactic acid-co-Glycolic Acid Polyol (LLA-GA)

Materials

Glycolic acid (GA), L-lactic acid (LLA) and 1,4-butanediol (BDO) were used as received. Lactic acid-co-glycolic acid polyol was prepared according to the following procedure.

Method

Glycolic acid (142.17 g, 70% in water), l-lactic acid (1205.6 g, 88% in water) and BDO (75.10 g) were weighed in to a 3 L five-neck round bottom flask. The flask was fitted with a condenser, nitrogen inlet, thermometer, magnetic stirrer bead and the set up was placed in an oil bath. The oil bath was gradually heated to 190° C. The reaction was stopped after 72 h.

The acid number and hydroxyl number of the polyol was determined according to methods ASTM D1980-87 and ASTM E1899-02, respectively. The molecular weight of the polyol was 1033.1 based on hydroxyl number (106.09) and the acid number was 2.516.

Step 2: Preparation of a Polyurethanes Series with Varying Hard Segment Percentage Materials BDO was dried at 70° C. under vacuum (0.1 torr) to reduce moisture content below 200 ppm prior to use in the synthesis. HDI, IPDI and stannous octoate were used as received. Polyol (PLLA:GA, MW 1033.1) was dried under vacuum (0.01 torr) until less than 200 ppm water prior to use in polymerisation.

Method

The following procedure illustrates the preparation of a polyurethane with 80% hard segment by one-step method.

The polyol (10.0000 g) and BDO (11.3409 g) were accurately weighed into a glass beaker. The beaker was covered with aluminium foil and placed in a dry nitrogen oven at 70° C. IPDI (24.1001 g) and HDI (4.5590 g) were weighed into a wet-tared polypropylene beaker, covered with foil and placed in the dry nitrogen oven at 70° C. Once the beakers had reached temperature, the isocyanate mixture was added to the polyol and BDO mixture and stirred manually until the mixture became homogenous. Stannous octoate (0.05% of the total mass) was added with stirring. The viscous reaction mixture was poured onto a Teflon tray once the reaction exotherm had reached its completion and left overnight in an 80° C. oven in a nitrogen atmosphere.

Using a similar procedure, polyurethanes with 60, 70, 90 and 100% hard segment were prepared using the quantities of reagents shown in Table 1.

TABLE 1

Formulation details of samples prepared according to procedure in Example 1

| Sample Code | Hard Segment (%) | IPDI (g) | HDI (g) | BDO (g) | Polyol LLA-GA (g) |
|---|---|---|---|---|---|
| 1-1 | 60 | 18.7181 | 3.5408 | 7.7411 | 20.0000 |
| 1-2 | 70 | 21.4091 | 4.0499 | 9.5410 | 15.0000 |
| 1-3 | 80 | 24.1001 | 4.5590 | 11.3409 | 10.0000 |
| 1-4 | 90 | 26.7912 | 5.0680 | 13.1408 | 5.0000 |
| 1-5 | 100 | 29.4822 | 5.5771 | 14.9407 | 0.0000 |

The polymers were compression molded to 100 micron thick sheets for preparing test specimens for tensile testing. Compression molding was carried out using a Wabash Melt Press at 190° C. Polymer pieces were placed between diamond-fusion glass plates within a 0.1 mm thick brass template and pressed up to 8 ton pressure to form a film at 190° C. Films were removed from the mold after cooling down and 5 mm×45 mm rectangular test strips were cut and annealed at 80° C. overnight under nitrogen. The test specimens were conditioned in water for 24 h at 37° C. before tensile testing.

Tensile tests were conducted according to ASTM D638 using Instron Universal Testing System Model 5568 equipped with Merlin 2002 software. The gauge length (cross-head distance) was 25 mm and the strain rate was 12.5 mm/min. unless indicated otherwise all mechanical properties were tested with specimens presoaked for 24 h at 37° C., in an environmental chamber at 37° C.

TABLE 2

Mechanical Properties of Polyurethanes Prepared in Example 1

| Sample code | UTS (MPa) | Stress @ Yield (MPa) | Modulus (MPa) | Elongation @ Break (%) |
|---|---|---|---|---|
| 1-1 | 30.8 ± 6.3 | 15.2 ± 5.0 | 1022 ± 293 | 209 ± 23 |
| 1-2 | 34.9 ± 5.0 | 18.5 ± 1.3 | 1487 ± 49 | 210 ± 41 |
| 1-3 | 45.9 ± 3.3 | 23.1 ± 0.7 | 1322 ± 103 | 285 ± 27 |
| 1-4 | 38.8 ± 1.3 | 25.4 ± 1.2 | 1206 ± 26 | 161 ± 42 |
| 1-5 | 48.5 ± 5.0 | 31.4 ± 3.7 | 1634 ± 172 | 164 ± 19 |

Test results based on testing at 37° C. in a 50% humidity environmental chamber with specimens that had been presoaked in water for 24 h at 37° C.

Example 2

This Example illustrates the preparation of polyurethanes by varying the molar ratio of HDI and IPDI while keeping the hard segment weight percentage constant at 60%. The soft segment polyol was P(LLA:GA):90:10 (MW 1033.1) and the chain extender was BDO.

Materials

BDO was dried at 70° C. under vacuum (0.1 torr) to reduce moisture content below 200 ppm prior to use in the synthesis. HDI, IPDI and stannous octoate were used as received. Polyol (PLLA:GA, MW 1033.1, prepared according to the method described in Example 1 was dried at 90° C. for 4 hours under vacuum (0.01 torr) prior to use in polymerisation.

Method

Four polyurethanes were prepared using the reagents as shown in Table 3. The following procedure was used to prepare sample 2-1 and a similar procedure was used to prepare other samples in the series except, the quantities of reagents used were different as shown in Table 3.

The method of polymerisation was the same as for Example 1 using the masses shown in Table 3.

TABLE 3

Formulation details of samples prepared according to procedure in Example 1

| Sample Code | HDI:IPDI (molar ratio) | IPDI (g) | HDI (g) | BDO (g) | Polyol LLA-GA (g) |
|---|---|---|---|---|---|
| 2-1 | 80:20 | 5.2438 | 15.8713 | 8.8849 | 20.0000 |
| 2-2 | 60:40 | 10.0823 | 11.4435 | 8.4742 | 20.0000 |
| 2-3 | 40:60 | 14.5608 | 7.3452 | 8.0940 | 20.0000 |
| 2-4 | 20:80 | 18.7181 | 3.5408 | 7.7411 | 20.0000 |

Test specimen preparation and tensile testing was conducted using the procedures described in Example 1.

TABLE 4

Mechanical properties of polyurethanes prepared according to Example 2

| Sample code | UTS (MPa) | Stress @ Yield (MPA) | Modulus (MPa) | Elongation @ Break (%) |
|---|---|---|---|---|
| 2-1 | 16.3 ± 2.1 | 0.49 ± 0.11 | 72 ± 25 | >300 |
| 2-2 | 43.0 ± 4.4 | 2.62 ± 0.24 | 231 ± 23 | >300 |
| 2-3 | 37.3 ± 5.5 | 2.34 ± 1.06 | 264 ± 71 | >300 |
| 2-4 | 30.8 ± 6.3 | 15.22 ± 5.00 | 1022 ± 293 | 209 ± 23 |

Test results based on testing at 37° C. in a 50% humidity environmental chamber with specimens that had been presoaked in water for 24 h at 37° C.

The material 2-2 from Example 2 was compression molded using the method described in Example 1 and tested at ambient temperature under dry conditions. The polymer exhibited UTS of 53.2±1.8 MPa, a modulus of elasticity of 2261±104 MPa and an elongation at break of 160±98%.

Example 3

This example illustrates a two-step polymerisation of a 1 kg batch of the polyurethane samples with sample code 1-3 described in Example 1 for evaluation of processability.

Materials

BDO was dried at 70° C. under vacuum (0.1 torr) prior to use in the synthesis. HDI, IPDI and stannous octoate were used as received. Polyol (PLLA:GA, MW 1033.1) was dried at under vacuum (0.01 torr) prior to use in polymerisation until less than 200 ppm water.

Method

The polyol (200.0 g) and BDO (90.72 g, 40% of required) were accurately weighed in a 2 L glass beaker. The beaker top was covered with aluminum foil and placed in the oven at 70° C. IPDI (482.0 g) and HDI (91.18 g) were weighed in to a separate wet-tared glass beaker and heated to 70° C. The isocyanate mixture was added to the polyol and BDO mixture and stirred manually until the mixture became homogenous. Stannous octoate (0.05 wt % of total mixture) catalyst was added to this while stirring constantly and the temperature of the reaction mixture was monitored using a thermocouple. Due to the reaction exotherm, the temperature increased. The reaction mixture was allowed to cool to 80° C. under nitrogen and remaining BDO (136.08 g) was added and stirred to form a homogenous mixture. Upon completion of the reaction exotherm, the viscous polymer solution was poured onto a Teflon tray and placed in an oven at 80° C. overnight under a nitrogen atmosphere.

The molecular weight (Mn) and polydispersity of the polymer determined by gel permeation chromatography was 111780 and 2.05, respectively.

The cured polymer was granulated, dried in a nitrogen circulating oven at 80° C. overnight and extruded to pellets.

A sample of polymer was analysed by differential scanning calorimetry (DSC) and the DSC trace is shown in the FIG. 1. The onset and mid point of the glass transition temperatures were 70° C. and 75° C., respectively.

Example 4

This example illustrates a polymer made incorporating a degradable chain extender.

Materials

BDO was dried at 70° C. under vacuum (0.1 torr) prior to use in the synthesis. HDI, IPDI and stannous octoate were used as received. Polyol (PLLA:GA, MW 1033.1) was dried at 90° C. for 4 hours under vacuum (0.01 torr) prior to use in polymerisation. Degradable chain extender Lactic acid-Ethylene glycol ester diol (LA-EG) was prepared using the following procedure.

Methods

1-Lactic acid (56.7 g) was placed in a 1 L round bottom flask fitted with a nitrogen inlet, condenser and a magnetic stirrer bar. The flask was placed in an oil bath and heated to 220° C. for 5 hours to distil off condensed water. The resulting product, polylactic acid was collected from the flask as a white solid. Poly(lactic acid) (43 g) and ethylene glycol (283.6 g) was heated in a 1-L round bottom flask at 200° C. for a period of 17 hours. The LA-EG ester diol was purified by distillation of the reaction product using Kugelrohr apparatus at 50° C. under vacuum (0.01 to 0.0001 torr). The LA-EG fraction was collected and redistilled for further purification. The purified LA-EG was a clear liquid and the reaction yield was 53%.

Polyurethane synthesis: PLLA:GA polyol 9.8430 g, MW 1067.6, prepared according to method in Example 1 was weighed into a glass beaker and BDO (5.3066 g) and LA-EG (7.8981 g) degradable chain extender were added. The beaker was covered with an aluminium foil and warmed to 70° C. IPDI (20.3523 g) and HDI (6.6000 g) were weighed into separate wet-tared polypropylene beakers and warmed to 70° C. The isocyanate mixture was added to the polyol mixture and stirred using a spatula until the mixture became homogeneous. Stannous octoate (0.0253, 0.05 wt % of total mass) was added to the mixture and stirred vigorously and when the solution had increased in viscosity, it was poured onto a Teflon tray and cured at 80° C. under nitrogen to complete the polymerisation.

The number average molecular weight and polydispersity were 54120 and 1.96, respectively based on GPC analysis.

The mechanical properties of the polymer were determined using the procedure described in Example 1. The polymer exhibited 34.4±9.4 MPa UTS, 1314±353 MPa modulus of elasticity, 15.7±5.7 MPa stress @ yield and 223±50% elongation at break.

Example 5

Materials

DL-lactic acid (DLLA) and butanediol (BDO) were used as received. Polyol (DLLA MW 1027.33) was dried at 80° C. under vacuum (0.1 torr) until less than 200 ppm water. Poly DLLA polyol was prepared according to the following procedure.

Method

DL-lactic acid (3854 g, 90% in water) and BDO (225.3 g) were weighed in to a 5 L five-neck round bottom flask. The flask was fitted with an overhead stirrer, condenser, nitrogen inlet and thermometer and the set up was placed in an oil bath. The stirrer speed was set to 150±5 rpm and the oil bath was gradually heated to 180° C. Part of the flask above the oil surface was covered with aluminium foil to reduce heat loss and to maintain a constant rate of distillation of water. The reaction mixture became clear and homogeneous after stirring for about 30 min. Heating and stirring were maintained and acid number was monitored after 48 h of reaction. When the acid number of the reaction mixture reached 4.095 the reaction was stopped and allowed the product to cool to ambient temperature.

The acid number and hydroxyl number of the polyol was determined according to ASTM methods ASTM D1980-87 and ASTM E1899-02, respectively. The molecular weight of the polyol was 1027.33 based on hydroxyl number (105.3) and the acid number was 4.095.

Materials

BDO was dried at 70° C. under vacuum (0.1 torr) prior to use in the synthesis. HDI, IPDI and stannous octoate were used as received. Polyol (PDLLA 1027.33) was dried at 80° C. under vacuum (0.01 torr) until less than 200 ppm water prior to use in polymerisation.

Method

The polyol (9.8866 g) and BDO (11.2090 g) were accurately weighed into a 150 mL Bomex glass beaker. The beaker was covered with aluminium foil and placed in the oven at 70° C. for 15-30 mins. IPDI (24.3064 g) and HDI (4.5980 g) were weighed into a separate wet-tared glass Pyrex beaker, covered with aluminium foil and heated to 70° C. for 10-15 mins. Polyol and BDO mixture was first stirred and mixed well. The isocyanate mixture was then added to the polyol/BDO mixture and stirred manually until the mixture became homogenous. Stannous octoate (0.05 wt % of total mixture) catalyst was added to this while stirring constantly until the mixture became very viscous and hot. The viscous polymer solution was poured onto a Teflon tray and placed in an oven at 100° C. overnight for 18 hrs under nitrogen.

The mechanical properties of the polymer were determined at 37° C. using the procedure described in Example 1. The polymer exhibited 39.8±8.0 MPa UTS, 1501±21 MPa modulus of elasticity, 17.9±2.4 MPa stress @ yield and 212±154% elongation at break.

Example 6

This example illustrates the degradation of polyurethanes under accelerated test conditions.

Materials and Methods

Polyurethanes 1-3, 1-5 (prepared in Example 1), and polyurethane prepared in Example 4 and 5 were used in this study.

All four polyurethanes were compression molded to 100 micron thick sheets for preparing test specimens for the study. Compression molding was carried out using a Wabash Melt Press at 190° C. Polymer pieces were placed between diamond-fusion glass plates within a 0.1 mm thick brass template and pressed to up to 8 ton pressure to form a film at 190° C. Films were removed from the mold after cooling down and 5 mm×45 mm rectangular test strips were cut and annealed at 80° C. overnight under nitrogen gas.

Three strips from each polymer were placed in separate glass vials and filled with PBS buffer (pH 7.4±0.2) to completely cover the strip. The capped vials were placed in an incubating oven at 70° C. Samples were removed from the oven after two weeks, allowed to cool down to room temperature and allowed to condition in de-ionised water for 2 to 3 days to completely remove any salts from buffer solution. The washed strips were dried at 40° C. for 4-5 days and weighed accurately to determine mass loss. Table 5 shows mass loss data under the accelerated degradation test conditions.

TABLE 5

| Mass loss under accelerated test conditions | |
| --- | --- |
| Polymer Sample | Mass Loss (%) |
| 1-3 | 19.2 ± 0.3 |
| 1-5 | 15.4 ± 2.9 |
| Example 4 | 17.8 ± 3.9 |
| Example 5 | 9.9 ± 3.6 |

Example 7

Polyurethane prepared in Example 3 was used in this experiment. Test specimens were prepared according to the procedure described in Example 1. This example illustrates that the polyurethanes also exhibit high modulus and elongation when tested at a temperature higher than normal body temperature.

The mechanical properties of the polymer were determined using the procedure described in Example 1; however the test temperatures were 37° C. and 40° C. The polymer properties and test conditions are shown in Table 6.

TABLE 6

Tensile properties of polymer prepared in Example 3

| Test conditions | | | Mechanical properties | | |
|---|---|---|---|---|---|
| | | | Stress @ | | Elongation |
| Temp (° C.) | Sample condition | UTS (MPa) | Yield (MPa) | Modulus (MPa) | @ break (%) |
| 40 | Wet | 25.9 ± 5.8 | 13.8 ± 2.2 | 1144 ± 285 | 100 ± 55 |
| 37 | Wet | 35.12 ± 3.9 | 21.4 ± 3.8 | 1630 ± 93 | 123 ± 67 |

Example 8

Materials

BDO was dried at 70° C. under vacuum (0.1 Torr), Polyol (LLA-GA 1033.1) was prepared as per Example 1 and degassed under vacuum before use, IPDI and stannous octoate, were used as received.

Method

The BDO and polyol were accurately weighed into a glass beaker. The beaker was covered with aluminium foil and placed in a dry nitrogen oven at 70° C. IPDI was weighed into a wet-tared glass beaker, covered with foil and placed in the dry nitrogen oven at 70° C. Once the beakers had reached temperature, the IPDI was added to the BDO/polyol and stirred manually until the mixture became homogenous. Stannous octoate (0.05% of the total mass) was added with stirring. The viscous reaction mixture was poured onto a Teflon tray once the reaction exotherm had reached its completion and left overnight in an 80° C. oven in a nitrogen atmosphere. A series of four polyurethanes were prepared with the formulation details shown in Table 7.

TABLE 7

Formulation details of polymers prepared in Example 8

| Sample Code | Hard Segment % | IPDI (g) | BDO (g) | Polyol LLA-GA (g) |
|---|---|---|---|---|
| 8-1 | 40 | 16.0927 | 3.9073 | 30.0000 |
| 8-2 | 50 | 19.3401 | 5.6599 | 25.0000 |
| 8-3 | 60 | 22.5874 | 7.4126 | 20.0000 |
| 8-4 | 70 | 25.8347 | 9.1653 | 15.0000 |

TABLE 8

Molecular weight and glass transition temperature

| Sample Code | Hard Segment % | Mn | Mw | Tg (mid, ° C.) |
|---|---|---|---|---|
| 8-1 | 40 | 53596 | 82759 | 63.07 |
| 8-2 | 50 | 46387 | 70406 | 66.63 |
| 8-3 | 60 | 57361 | 87943 | 71.48 |
| 8-4 | 70 | 79162 | 132567 | 78.27 |

The polymers were melt pressed into a 100 μm film, strips cut (5 mm×50 mm) and then oriented by first heating a hot air gun and then extending manually to approx, 100% of initial length. A 40 mm length of each drawn polymer was measured and placed in distilled water at 37° C. for 20 hours. After 20 hours the strips were remeasured to assess percentage shrinkage.

TABLE 9

The effect of polymer composition on shrinkage

| Sample Code | Length | % shrinkage |
|---|---|---|
| 8-1 | 31 mm | 22.5% |
| 8-2 | 31 mm | 22.5% |
| 8-3 | 36 mm | 10.0% |
| 8-4 | 39 mm | 2.5% |

Example 9

This example illustrates the preparation of two polyurethanes and subsequent accelerated degradation. The composition of the polymers is as follows:

TABLE 10

Formulation details

| Sample Code | Hard Segment % | Diisocyanate: IPDI (g) | Chain extender(s) (g) |
|---|---|---|---|
| 9-1 | 100 | 34.1958 | LA-EG (6.7431) BDO (9.0611) |
| 9-2 | 100 | 31.4155 | LA-EG (18.5845) |

Materials

BDO (Aldrich) was dried at 70° C. under vacuum (0.1 Torr), IPDI (Aldrich) and stannous octoate (Aldrich), were used as received. LA-EG was prepared as per Example 4 and dried at 50° C. under vacuum (0.1 Torr).

Method

The chain extender(s) were accurately weighed into a glass beaker. The beaker was covered with aluminium foil and placed in a dry nitrogen oven at 70° C. IPDI was weighed into a wet-tared glass beaker, covered with foil and placed in the dry nitrogen oven at 70° C. Once the beakers had reached temperature, the IPDI was added to the chain extender(s) and stirred manually until the mixture became homogenous. Stannous octoate (0.05% of the total mass) was added with stirring. The viscous reaction mixture was poured onto a Teflon tray once the reaction exotherm had reached its completion and left overnight in an 80° C. oven in a nitrogen atmosphere.

Fibres of Polymer 9-1 were extruded and the mechanical properties were measured by an Instron Universal Testing System Model 5568 equipped with Merlin 2002 software: Tensile Modulus=2274 MPa±308; elongation at break 163 MPa±13; UTS 200 MPa±15. The diameter of the fibres was 117±4 micron.

Degradation: The polymers were cut into small pieces and weighed out for the degradation test. The polymers were weighed into individual round-bottomed flasks (5.0531 g of 10-1 and 4.9996 g of 10-2), 250 ml of deionised water added to each and each round-bottomed flask fitted with a vertical condenser and magnetic Teflon® stirrer bead and set to reflux on a heated oil bath.

The polymer residue was sampled at various time points and analysed by GPC (THF).

TABLE 11

Accelerated degradation study

| | Sample Code 9-1 | | | Sample Code 9-2 | | |
|---|---|---|---|---|---|---|
| Time (days) | Mn | Mw | PD | Mn | Mw | PD |
| 0 | 19103 | 30788 | 1.61 | 19806 | 34134 | 1.72 |
| 1 | 8236 | 14828 | 1.80 | 19105 | 35432 | 1.85 |
| 2 | 2767 | 5359 | 1.94 | 5986 | 13401 | 2.24 |
| 5 | 1167 | 1985 | 1.70 | 2161 | 4047 | 1.87 |
| 6 | 933 | 1604 | 1.72 | 1998 | 3627 | 1.82 |
| 7 | 790 | 1299 | 1.64 | 2004 | 3339 | 1.67 |
| 8 | 701 | 1252 | 1.78 | 1789 | 3114 | 1.74 |
| 9 | 617 | 933 | 1.51 | 1750 | 2979 | 1.70 |
| 12 | 528 | 694 | 1.31 | 1652 | 2765 | 1.67 |

Example 10

Real Time Degradation Study

Materials and Methods

Polyurethanes 1-3, 1-5 (prepared in Example 1), and polyurethane prepared in Example 4 and 5 were used in this study.

Test specimens for the study were prepared according to the method described in Example 6.

For each time point 10 test strips (5×4.5 mm) from each polymer were placed in separate glass vials and filled with PBS buffer (pH 7.4±0.2) to cover the strips completely. The capped vials were placed in a shaker incubator at 37° C. Samples were removed from the incubator at pre set time points, allowed to cool down to room temperature and conditioned in de-ionised water for 2 to 3 days to completely remove any salts from buffer solution. The washed strips were dried at 40° C. for 4-5 days and three samples weighed accurately to determine mass loss and the rest were used for testing mechanical properties. Table 7 shows mechanical properties over time.

TABLE 12

Mechanical properties during degradation

| Degradation Time | UTS (MPa) | Stress @ Yield (MPa) | Modulus of Elasticity (MPa) | Elongation @ break (%) |
|---|---|---|---|---|
| POLYMER 1-3 | | | | |
| 24 h | 53 ± 7 | 24 ± 7 | 1325 ± 278 | 293 ± 14 |
| 4 weeks | 41 ± 3 | 22 ± 2 | 1644 ± 55 | 204 ± 52 |
| 12 weeks | 36 ± 1 | 22 ± 2 | 1434 ± 133 | 173 ± 38 |
| 16 weeks | 38 ± 3 | 21 ± 2 | 1419 ± 67 | 223 ± 38 |
| 6 months | 19 ± 2 | 14 ± 1 | 967 ± 84 | 65 ± 63 |
| 9 months | 30 ± 1 | 21 ± 0 | 1495 ± 47 | 59 ± 60 |
| 12 months | 38 ± 2 | 2 ± 1 | 830 ± 350 | 238 ± 35 |
| POLYMER 1-5 | | | | |
| 24 h | 47 ± 3 | 31 ± 2 | 1723 ± 284 | 18 ± 8 |
| 4 weeks | 49 ± 3 | 32 ± 2 | 1585 ± 37 | 149 ± 48 |
| 12 weeks | 49 ± 3 | 33 ± 4 | 1798 ± 119 | 21 ± 3 |
| 16 weeks | 48 ± 4 | 40 ± 4 | 2125 ± 169 | 10 ± 1 |
| 6 months | Not tested | | | |
| 9 months | Not tested | | | |
| 12 months | Not tested | | | |
| Polymer in Example 4 | | | | |
| 24 h | 35 ± 6 | 14 ± 5 | 1027 ± 305 | 253 ± 30 |
| 4 weeks | 31 ± 5 | 13 ± 2 | 1162 ± 101 | 205 ± 38 |
| 12 weeks | 29 ± 6 | 18 ± 4 | 1372 ± 205 | 142 ± 52 |
| 16 weeks | 23 ± 4 | 12 ± 2 | 1246 ± 116 | 119 ± 68 |
| 6 months | 5 ± 3 | 5 ± 4 | 620 ± 205 | 1.5 ± 0 |
| 9 months* | 8 | 7 | 575 | 1.8 |
| 12 months | Not able to measure properties due to degradation | | | |
| Polymer in Example 5 | | | | |
| 24 h | 43 ± 3 | 23 ± 4 | 1203 ± 175 | 291 ± 19 |
| 4 weeks | 44 ± 3 | 23 ± 4 | 1506 ± 128 | 282 ± 18 |
| 12 weeks | 43 ± 5 | 21 ± 1 | 1507 ± 91 | 299 ± 17 |
| 16 weeks | 43 ± 6 | 21 ± 2 | 1408 ± 100 | 267 ± 41 |
| 6 months | 30 ± 10 | 23 ± 5 | 1095 ± 118 | 12 ± 6 |
| 9 months | 29 ± 1 | 19 ± 2 | 1253 ± 83 | 203 ± 38 |
| 12 months | 30 ± 10 | 14 ± 2 | 756 ± 129 | 221 ± 108 |

*Only one specimen measured due to fragile samples as a result of degradation

Example 11

Polymer 1-3 prepared in Example 1 was remade by reactive extrusion into fibres of diameter 0.20-0.35 mm under different extrusion conditions and draw ratios. The fibres were cut to 100 mm lengths and placed into water at 37° C. and fiber length measured over time. After 6 days the fibres had shrunk between 0% and up to 7% (Table 13).

TABLE 13

Length of fibres over time in water at 37° C.

| | Time | | |
|---|---|---|---|
| | 0 | 16 hours | 6 days |
| 11-1 | 100 mm | 99.0 mm | 93.0 mm |
| 11-2 | 100 mm | 99.5 mm | 98.0 mm |
| 11-3 | 100 mm | 101.0 mm | 100.0 mm |
| 11-4 | 100 mm | 100.5 mm | 98.0 mm |

Example 12

BDO (Aldrich) was dried at 70° C. under vacuum (0.1 Torr), HDI (Fluka), trans-1,4-cyclohexane diisocyanate (CHDI, Synthon Chemicals, Germany) and dibutyl tin dilaurate (DBTL, Aldrich), were used as received.

Method

The CHDI and HDI and DBTL were weighed into a beaker and mixed well at 80° C. before adding to a preheated syringe pump which provided heating at 85° C. BDO was dried overnight under vacuum before adding to a second syringe pump. The syringe pump containing the isocyanates and catalyst and the syringe pump containing the BDO both injected at the appropriate mass flow rate into a reactive extruder where the polymerisation took place and extruded into fibres.

TABLE 14

Formulation details

| Sample Code | Hard Segment % | CHDI | HDI | BDO |
|---|---|---|---|---|
| 12-1 | 100 (1.02 NCO index) | 16.2260 g | 49.2666 g | 34.5074 g |

TABLE 15

Tensile properties of both the unoriented and the oriented (drawn by hand with heat) fibres

| Degradation Time | UTS (MPa) | Modulus of Elasticity (MPa) | Elongation @ break (%) |
|---|---|---|---|
| 12-1 (unoriented) | 54 ± 22 | 634 ± 125 | 226 ± 107 |
| 12-1 (oriented) | 343 ± 107 | 2225 ± 682 | 47 ± 16 |

What is claimed is:

1. A polyurethane or polyurethane/urea composition which has a tensile strength greater than 10 MPa, a modulus of elasticity greater than 400 MPa and an elongation at break greater than 150% at a temperature of between 0° C. and 60° C. and at a relative humidity of between 0% and 100%, wherein the polyurethane or polyurethane/urea composition is derived from diisocyanate, and a polyol having the formula:

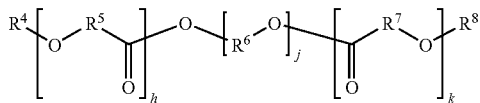

wherein only one of h or k can be zero or both are integers other than zero, j is zero or an integer other than zero, $R^4$ and $R^8$ are independently selected from the group consisting of hydrogen, hydroxylalkyl, aminoalkyl, and carboxyalkyl, $R^5$, $R^6$ and $R^7$ cannot be hydrogen, but are independently a linear or branched alkyl, alkenyl, aminoalkyl, alkoxy or aryl, $R^5$ and $R^7$ are the same or different and distributed alternately, randomly or as blocks within the polyol structure;

wherein the polyurethane or polyurethane/urea composition comprises one or more chain extenders, at least one of which is a linear aliphatic glycol having a molecular weight less than 350, and wherein the polyurethane or polyurethane/urea composition is biocompatible and biodegradable.

2. The polyurethane or polyurethane/urea composition of claim 1 comprising at least two polyurethanes and/or polyurethane/ureas having different glass transition temperatures.

3. The polyurethane or polyurethane/urea composition of claim 1 wherein the composition is derived from at least two diisocyanates at least one of the diisocyanates containing isocyanate moieties in an unsymmetric configuration.

4. The polyurethane or polyurethane/urea composition of claim 3 wherein at least one of the diisocyanates contains isocyanate moieties in a symmetric configuration.

5. The polyurethane or polyurethane/urea composition of claim 1 wherein the composition is derived from at least two diisocyanates at least one of the diisocyanates containing isocyanate moieties attached to a cyclic structure.

6. The polyurethane or polyurethane/urea composition of claim 5 wherein at least one of the diisocyanates contains isocyanate moieties attached to a linear structure.

7. The polyurethane or polyurethane/urea composition of claim 1 additionally comprising one or more chain extenders.

8. The polyurethane or polyurethane/urea composition of claim 7 wherein at least one of the chain extenders has a hydrolysable linking group.

9. An article of manufacture formed from the polyurethane or polyurethane/urea compositions of claim 1.

10. The article of claim 9 wherein the article is a medical device, an orthopedic implant, a bone fixation device, a vascular stent, a spinal cage or a scaffold.

11. The polyurethane or polyurethane/urea composition of claim 1, wherein the linear aliphatic glycol is a $C_2$-$C_{10}$ linear aliphatic glycol.

12. The polyurethane or polyurethane/urea composition of claim 1, wherein the linear aliphatic glycol is ethylene glycol, diethylene glycol, tetraethylene glycol, 1,3-propane diol, 1,4-butane diol, 1,6-hexanediol, 1,7-heptanediol, 1,8-octanediol, 1,9-nonanediol, or 1,10-decanediol.

13. The polyurethane or polyurethane/urea composition of claim 1, wherein the composition comprises a hard segment representing 40 to 100% by weight of the composition.

14. The polyurethane or polyurethane/urea composition of claim 3, wherein the at least one diisocyanate containing isocyanate moieties in an unsymmetric configuration is selected from the group consisting of isophorone diisocyanate, toluene diisocyanate, lysine diisocyanate ethyl ester and lysine diisocyanate methyl ester.

15. The polyurethane or polyurethane/urea composition of claim 4, wherein the at least one diisocyanate containing isocyanate moieties in a symmetric configuration is selected from the group consisting of 1,6-hexamethylene diisocyanate, trans-cyclohexane diisocyanate, 1,4-butanediisocyanate, 1,2-ethanediisocyanate, 1,3-propanediisocyanate, para-tetramethyl xylene diisocyanate, 4,4'-methylene diphenyldiisocyanate, 1,4-naphthalene diisocyanate, para-phenylene diisocyanate, 4,4'-methylene-bis(cyclohexyl isocyanate), meta-tetramethyl xylenediisocyanate and cis-cyclohexanediisocyanate.

16. The polyurethane or polyurethane/urea composition of claim 1, wherein the composition is extrusion processed.

17. The polyurethane or polyurethane/urea composition of claim 16, wherein the composition is extrusion processed into fibres.

18. The polyurethane or polyurethane/urea composition of claim 17, wherein the fibres are oriented.

19. The article of claim 9 wherein the article is formed from extrusion processed fibres.

20. The polyurethane or polyurethane/urea composition of claim 1 further comprising cells and/or growth factors.

21. The polyurethane or polyurethane/urea composition of claim 20 wherein the cells are progenitor cells.

22. The polyurethane or polyurethane/urea composition of claim 1 further comprising pharmaceuticals for use in drug delivery.

23. The polyurethane or polyurethane/urea composition of claim 8 further comprising pharmaceuticals for use in drug delivery.

24. The polyurethane or polyurethane/urea composition of claim 1 further comprising a substance selected from the group consisting of barium sulphate, barium carbonate, halogen-containing compounds, tricalcium phosphate, hydroxyapatite or gold.

* * * * *